United States Patent
Aaltonen et al.

[11] Patent Number: 5,993,413
[45] Date of Patent: Nov. 30, 1999

[54] INTRAORAL ADMINISTRATION DEVICE AND SYSTEM

[76] Inventors: Antti Sakari Aaltonen, Marttilantie 2as.6, FIN-03850 Pusula, Finland; Jouko Suhonen, 663 Garth Ct., Yorktown Heights, N.Y. 10598

[21] Appl. No.: 09/068,394
[22] PCT Filed: Nov. 11, 1996
[86] PCT No.: PCT/FI96/00609
§ 371 Date: Sep. 3, 1998
§ 102(e) Date: Sep. 3, 1998
[87] PCT Pub. No.: WO97/17037
PCT Pub. Date: May 15, 1997

[30] Foreign Application Priority Data
Nov. 9, 1995 [FI] Finland ..................... 955389

[51] Int. Cl.⁶ .................................................. A61J 7/00
[52] U.S. Cl. .......................... 604/77; 128/859; 424/435; 433/37; 433/80
[58] Field of Search .................. 604/48, 54, 77, 604/514; 128/859–862; 424/435; 433/6, 37, 80, 88, 140

[56] References Cited

U.S. PATENT DOCUMENTS

| | | | |
|---|---|---|---|
| 3,840,992 | 10/1974 | English | 604/77 |
| 4,284,623 | 8/1981 | Beck. | |
| 4,324,782 | 4/1982 | Beck. | |
| 4,636,384 | 1/1987 | Stolle et al.. | |
| 5,017,372 | 5/1991 | Hastings. | |
| 5,127,903 | 7/1992 | Mailot et al. | 604/77 |
| 5,137,449 | 8/1992 | Goldin et al. | 433/229 |
| 5,395,392 | 3/1995 | Suhonen | 606/234 |
| 5,601,605 | 2/1997 | Crowe et al. | 606/236 |

FOREIGN PATENT DOCUMENTS

| | | |
|---|---|---|
| 0 389 224 | 9/1990 | European Pat. Off.. |
| 0 479 597 | 4/1992 | European Pat. Off.. |
| WO 91/04727 | 4/1991 | WIPO. |

OTHER PUBLICATIONS

J. Suhonen et al., "Release of Preventive Agents from Pacifiers in Vitro. An Introduction to a Novel Preventive Measure," Schweiz. Monatsschr. Zahnmed., 1994, 104;945–51.

Primary Examiner—Corrine McDermott
Assistant Examiner—LoAn H. Thanh
Attorney, Agent, or Firm—Evenson, McKeown, Edwards & Lenahan PLLC

[57] ABSTRACT

An intraoral administration device having an elongated, substantially plate-like arcuate oral screen designed to conform to the teeth and intended to be accommodated in the space between the teeth and the lips. The oral screen includes containers for the agent to be administered intraorally, which containers have provision for allowing the free entrance of saliva into the container and its exit therefrom. An administration system using the administration device and an active agent, such as for example an agent against caries or otitis media is also contemplated.

17 Claims, 5 Drawing Sheets

INTRAORAL ADMINISTRATION DEVICE AND SYSTEM

The object of the present invention is an intraoral administration device comprising an elongated, substantially plate-like curved oral screen designed to conform to the teeth and intended to be positioned in the space between the teeth and the lips. The object of the present invention is also an administration system, which comprises the administration device according to the invention in combination with an active agent.

By means of the administration system according to the invention it is possible to provide a sustained local therapeutic effect in the region of the mouth and throat which is adapted to take into account the eruption order of the teeth and the location of the salivary glands, while simultaneously satisfying the physiological sucking need and craving for sweetness of small children, using small dosage levels tolerated by children and without causing malocclusions, especially when the sucking need of the child continues too long from the orthodontic point of view.

Various dispensing pacifiers are known (for example U.S. Pat. No. 4,078,566, GB-patent application 2 181 957A; EP Pat. No. 0 494 904, FI-patent application FI-A 921411, U.S. Pat. No. 5,395,392; and the commercially available CANNON babysafe Minifeeder). Suhonen (1992) has presented the theoretical background for the use of a pacifier like administration device which slowly releases fluorides, xylitol, monoclonal caries antibodies or lactoperoxidase enzyme components into the mouth, in a prophylactic method for the prevention of dental caries. The operability of a dispensing pacifier for releasing sodium fluoride, xylitol and sorbitol from a tablet has been established in vitro, and the administration from a pacifier of passive vaccines against microbes causing oral diseases has been suggested (Suhonen at al, 1994). A pacifier prototype for dispensing sodium fluoride, xylitol and sorbitol has in our field trial with children of the age of 16 months proved to be a functioning weans with potential for development for the treatment of diseases of the mouth and throat of children in the sucking-age. In our follow-up study it also became evident that in the group of children that had accepted the test pacifier, there appeared significantly less often infection of the middle ear (otitis media, 48% versus 70%) than in the comparison group. Recently it has been shown that xylitol also inhibits the growth of *Streptococcus pneumoniae* (pneumococcus) (kontiokari et al 1995). According to one report (October 1996) the use of a xylitol bubble gum several times a day has reduced infection in the middle ear in kindergarten children in Oulu. The mouth cavity can thus be an area of primary defense in the battle against bacteria aiming for the middle ear.

In the continuous follow-up of our study cohort, it has been established that malocclusions in children using a pacifier become significantly more common when the use of the pacifier continues beyond the age of two. For this reason, taking into account the individual dentoalveolar jaw development, the pacifier should be given up at the stage of eruption of the deciduous molars which, on an average, coincides with that age, at which stage the sucking-need of a child optimally should already have changed into a chewing-need (Laitinen 1995). To prevent malocclusions Varrela and Alanen (1995) have presented an extensive pacifier study with an aim at finding a pacifier model which broadens the dental arch of the upper jaw. Prolonged pacifier sucking has also been alleged to cause middle ear infection (Niemelä 1984). On the other hand, if the pacifier is taken away from a child too early, he easily becomes a thumb-sucker which, from the point of view of bite development, is an even worse habit than sucking a pacifier. Also deciduous dentition destroyed by early caries attack cause displacements and malocclusion of the permanent teeth.

According to the invention, an administration device of the oral screen type has now been developed, by means of which an active agent can be slowly released into the mouth of a child, especially after the pacifier stage, in a manner preventing deformation of occlusion.

The invention is based on a so-called oral screen, that is an elongated, substantially plate-like device with an arcuate longitudinal cross-section, to be inserted in the space between the lips and the teeth. The administration device is characterized in that the oral screen comprises containers for an intraorally administrable agent which containers are provided with means, such as holes or apertures, allowing the free entrance of saliva into the containers and its exit therefrom.

The oral screen (OS) is a device known in orthodantology which is kept in the space (vestibulum oris, VO) between the teeth (T) and the lips (L) to push backward front teeth protruding in an open bite caused by a pacifier, lip-sucking or visceral act of swallowing (FIG. 1). In addition to oral screens individually manufactured in a dental laboratory, serially produced screens of different size are available, which are provided with a ring and are elastic or made from a harder plastics material (the first ones were made in 1956, the material being polyamide, Dr. E. Sch önherr, Radebeul. DDR; presently known manufacturers: Dentaurum, Germany; Dentamar, Holland, Myofunctional Research Co., Australia), which are sold and used for the main indication of strengthening poorly developed lip muscles and for breaking detrimental habits. It is known to provide the screen with additional means for guiding the position of the tongue or prominences for guiding the bite, such as a cap for the lower front teeth to bite into (Prof. R. Hinz, Herne, West-Germany, material "Duralan", year 1974; DE 3 840 178 A1). In a distal occlusion, the cap facilitates in keeping the device in place and accommodates the masticatory muscles so that growth is possible in the condyle area, which in favourable instances, in addition under the control of the inclined plane or the cap, moves the lower jaw permanently forward in an orthognathicly more correct position with respect to the skull base. Also a combination of an oral screen and a sucking piece of a pacifier is known (CH-patent 662 271 A5). There is need for orthodontic prophylaxis (Laitinen 1995, Verrela and Alanen 1900). There is, however, one problem with respect to taking an oral screen into use, namely pacifier users under the age of 3 and thumbsuckers under the age of 4 do not want to keep it in the mouth. When training the use of an oral screen, it can in a transitional period, in order to facilitate the adaptation process, initially be provided with a pacifier-like sucking piece which is acceptable to the child. One should, however, relatively soon get rid of the model provided with a sucking piece.

According to our invention, an oral screen of the known type has been provided with containers for the agent to be released into the mouth. One idea according to our invention is that when a good tasting substance, for example non-cariogenic xylitol (X) is placed in the dispensing containers in the cheek flanges of the oral screen (OS), and the xylital slowly dissolved primarily under the effect of saliva secreted from the glandula parotidea (parotid saliva, PS) gives the children a pleasant taste sensation (FIG. 2), such a device can be used to wean already a 2-year old child from teeth-damaging sucking habits, such as a sweet bottle, pacifier and perhaps also thumbsucking. As it, in addition, prevents mouth breathing (Darby 1890), the nose cavities are enlarged and remain open more easily, reducing simultaneously the risk for middle ear infection. Xylitol as such prevents middle ear infection (Uhari et al 1996). In mouth breathers, when the mouth is open, the stretched strong cheek muscles compress and flatten the upper jaw bone, whereby crossbites are easily developed on the sides. The oral screen removes the pressure of the muscles on the upper dental arch, allowing the arch to broaden freely, for example pushed by the pressure exerted by the tongue when swallowing. The taste buds in the tongue tip are sensitive to sweet. When the substance containers according to the invention are placed in the back and to the sides near the parotid gland duct (FIG. 2), the sweetener dissolved by the saliva (Xd) makes the child instinctively move the tip of the tongue. The pressure of the tongue resulting therefrom should reduce the risk for crossbites at the canine tooth area.

A suitable sweetening agent for use in the said application would be, for example, xylitol, which per se has several beneficial effects on the teeth (Arends er al. 1984, Mühlemann et al. 1970, Mäkinen 1978, Mäkinen and Isokangas 1988, Mäkinen and Scheinin 1982, Scheinin and Mäkinen 1975, Söderling and Pihlanto-Leppälä 1989, Söderling and Scheinin 1991, Touster 1960). Further possible non-cariogenic sweetening agents for the said use are i.a. saccharin, acesulfam-K, cyclamate, aspartame, alitame, thaumatins, rebaudocides, glycyrrhizin, sucralose and neohesperidin dihydrocalcone, although some of these are restricted in use and for others the safety testing and practical experience are still insufficient (Granby 1991).

Xylitol is not able to cause bacterial acid production wherefore it is a cariostatic agent (Mühlemann et al. 1970, Scheinin and Mäkinen 1975). In addition to the said cariostatic effect xylitol possesses apparent bacterial adhesion and accumulation inhibiting properties, and consequently it can reduce caries and middle ear infection in long term and frequent administration (Mäkinen 1978, Isokangas 1994, Kontiokari et al 1995, Uhari et al. 1996). Contrary to, for example sorbitol, xylitol causes in bacteria a so called "futile xylitol cycle" which uses much energy (Söderling and Pihlantoo-Leppälä 1989). Many so called xylitol products contain more than 30% sorbitol. Such products should not be used in our administration system, unless they are used together with further effective caries inhibitors, such as sodium fluoride. The Xylitol-Fludent fluoride tablet which is in general use in Finland, contains sorbitol 50%. Due to its sweet taste, children usually take it eagerly, and due to its sodium fluoride content it is suitable for use in the administration device according to the invention. By applying the oral screen strategy, it is possible to create for hours an oral fluid environment around the erupting teeth, which according to our studies have apparent caries preventing properties. Care has to be taken that the sweetening or other agents used are not cariogenic, i.e. do not cause caries. Preparations, wherein the proportion of xylitol as a sweetening agent is over 70%, can usually be held as cariostatic and safe for the teeth. A disadvantage of xylitol and other polyols is, however, their slow absorption from the intestine, especially in small children, whereby large doses can lead to osmotic diarrhea.

It is generally believed that the fluoride ion does not under normal conditions affect the colonization or mutans streptococci (Ms) (Kilian et al. 1979, van Houte et al. 1978, Zickert and Emilson 1982). According to one theory, however, the fluorides, at least at stronger concentrations, prevent the bacteria from adhering to the tooth surface by reducing the adhering electrostatic forces (Rölla 1977a). Usually the caries-preventing effect of fluorides on the teeth is associated with the capacity of the fluoride ion to harden the tooth surface and promote remineralization. In addition, the fluoride ion disturbs the carbohydrate metabolism of mutans streptococci and thus reduces the acid production in plaque (Hamilton 1977, Harper and Loesche 1986).

The adhesion of bacteria can be prevented also with substances of the lactin type, which have been found species-specifically i.e. in milk and in plant seeds (for example Neeser et al. 1988). Further optionally applicable agents are non-specifically antibacterial enzymes (Lenander-Lumikari 1992). One additional alternative is to add protecting agents in an amount sufficient to prevent the accumulation (aggregation) of plaque, acid production or other virulence factors, or use remineralizing agents which inhibit the damaging symptom of caries, demineralization of the tooth, of which agents the effect of the fluorides has been known for already half a century.

Interesting from the point of view of our inventive administration device are i.e. the caries antibodies produced in egg yolk (Sun GY, Taiyo Kagaku Co., Ltd, Japan) and the monoclonal mouse anti-mutans-streptococci antibodies (Ma and Lehner 1990, Ma et al. 1990). One relatively cheap method of producing antibodies is the so-called immune milk which method has been considered safe for human use. Immune milk can be produced by vaccinating a pregnant cow against certain pathogens, whereby the cow organism forms antibodies to these diseases, which are transferred to the colostrum. The remedying effects of immune milk are long known. Also known is a caries preventing cow immune milk product, which contains specific antibodies to killed streptococcus mutans—cells (U.S. Pat. No. 4,324,782). Immune milk has also been prepared against the cariogenic MS-species *S. sobrinus*, and the anti-MS-affect of an immune whey product has been studied also in vitro. The efficiency of a corresponding anti-S. mutans—whey product has been shown earlier in animal and human tests in adults (Michalek et al. 1987, Filler et al. 1991).

By means of an administration device which releases effective antibodies slowly into the mouth, a relatively sustained effect on the microflora of the mouth and throat is obtained with small doses. It is thus of importance that the used antibodies do not disturb the development of the normal flora which is important for the health of the mouth. As regards ear pathogenic pneumococci it is expected that an octavalent polysaccharide antigen vaccine conjugated to a protein carrier will to a large degree remove the problem of middle ear infection due to pneumococci (Gleblnk 1994). Thus *Heamophilus influenzae* (non-type b) and Branhamella (Moramxella) catarrhalis remain which are more difficult to treat and against which there is no known vaccine. Of these, the former is better known to its living habits. It has been shown already a long time ago that *H. influenzae* lives also in the south region, and its uncapsuled form (nontype b) is a quite common cause for recurrent middle ear infections in under 5 year olds. An IgG-antibody dispensed by the administration device against middle ear infection causing bacteria in a prophylactic manner could be surprisingly effective, even though the mechanisms are not known in detail (Kauppi et al. 1993).

An immune whey powder obtained from immune milk containing antibodies primarily of the IgG-type against middle ear infection contains also lactose, which stabilizes proteins and facilitates compressing of the powder into tablet form. It is possible to remove the lactose and replace the same at least partly with xylitol. An addition of xylitol would be beneficial because of the expected additive anti-caries and anti-otitis effect, and its protein stabilizing property.

It is in principle possible to make accurate monoclonal antibodies against any virulence factor of a microbe, after it has been identified, using known hybridoma and gene manipulation techniques. Perhaps the so far most promising anti-cariotic antibody preparation in the monoclonal IgGl-type antibody against the adhesive protein antigen SA I/II of the S. mutans cell wall (Ma et al. 1990). By treating the teeth with this antibody it has been possible to prevent the return of MS in the tooth plaque of adult humans (Ma and Lehner 1990).

Thus, in order to administer the afore mentioned and other active agents, an administration device is used according to the invention, which at the same time functions as an orthodontic oral screen preventing the development of jaw deformities. New in the invention is the fact that the active agent in a suitable manner is combined with the oral screen, suitably in containers in the oral screen or associated therewith, in which containers the agent can be introduced in the form of a tablet, lozenge mass or a cellulose, gelatin or nonwoven fabric disc (for example Fibrella, Suominen Oy, Nakkila, Finland) "impregnated" with the agent, and from which the active agent, for example through holes, is released into the oral cavity. The characteristics of the invention are given in the appended claims.

The administration device is preferably provided with a gripping means attached to the outer surface of the oral screen, that is to the surface facing the lips or the cheeks in use, the gripping means extending outside the mouth and which can also be provided with a gripping ring.

According to one embodiment of the invention, the container is formed by a recess made in the oral screen, especially in its end regions, that is in the cheek flanges, and a lid which at least partly covers the recess. If the oral screen is made from an elastic material, the said lid can be a strip-like member forming one piece with the oral screen, which at least partly covers the recess. If the oral screen is made from a hard material, the lid can be hinged to the oral screen and provided with suitable locking means, such as a suitable looking tongue.

The container can also be a cup-like, cage- or sieve-like construction opening outward from the surface of the oral screen, especially from its outer surface, and provided with a suitable lid.

According to a further embodiment, the container can be formed from a sheath-like member made from an elastic material and slid over the end part of the oral screen in a sealing engagement with the oral screen, which advantageously is provided with a loop member to be slid and tightened over the gripping means of the oral screen.

According to another alternative embodiment, the oral screen is in two-part form and comprises a so-called casing cover, the dispensing containers being arranged in the vicinity of the end regions of the said casing cover, which, in its longitudinal direction, is provided with a sliding slot extending from the center of the cover towards its end regions, and in addition, a sliding plate slidably mounted in a groove or recess in the inner surface of the cover, allowing the containers to be opened, to which plate gripping means are attached, which are slidably mounted in the sliding slot and extending outwards therefrom through the casing cover, as well as means for locking the sliding cover and the casing plate to each other.

In the following, reference is made to the appended drawings illustrating administration devices according to our invention. The Figures show:

Figure 4:
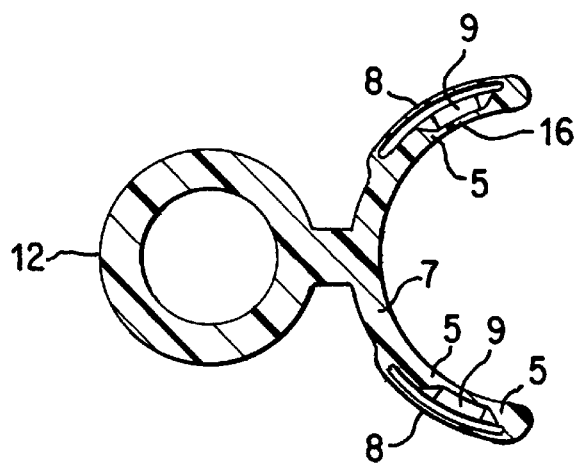

FIG. 4 the same in a horizontal longitudinal cross-section.

Figure 5:
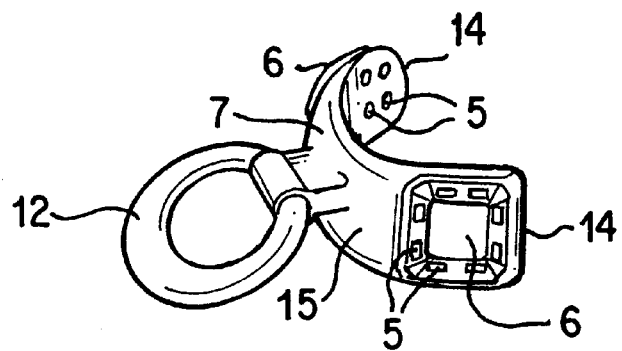

FIG. 5 illustrates an oral screen provided with pill containers with hinged lids, seen from in front, at an angle from above.

Figure 6:
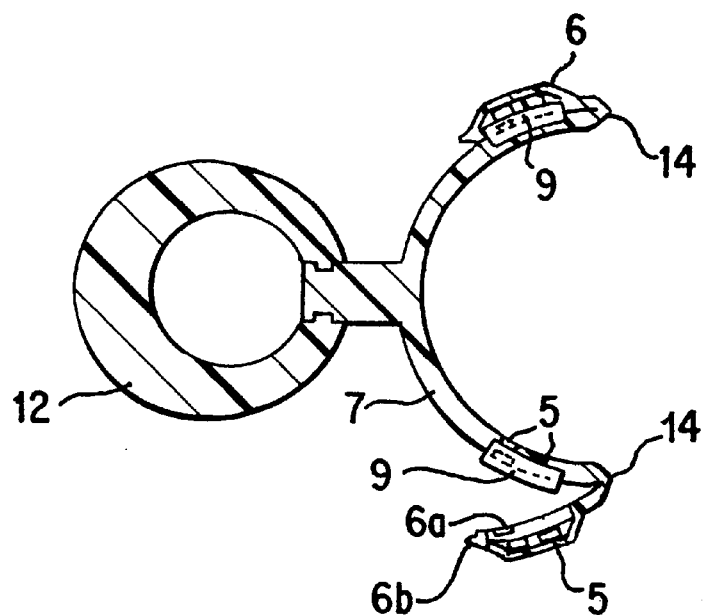

FIG. 6 the same as a horizontal longitudinal cross-section.

Figure 7:
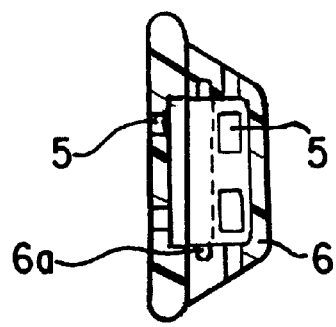

FIG. 7 illustrates the cross-section of a pill container with a hinged lid.

Figure 8:
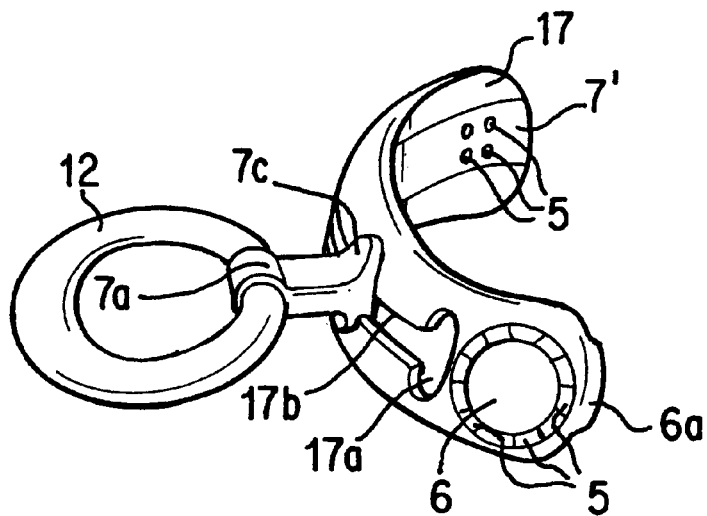

FIG. 8 illustrates an oral screen dispenser comprised of a sliding cover and casing plate seen from in front, at an angle from above.

Figure 9:
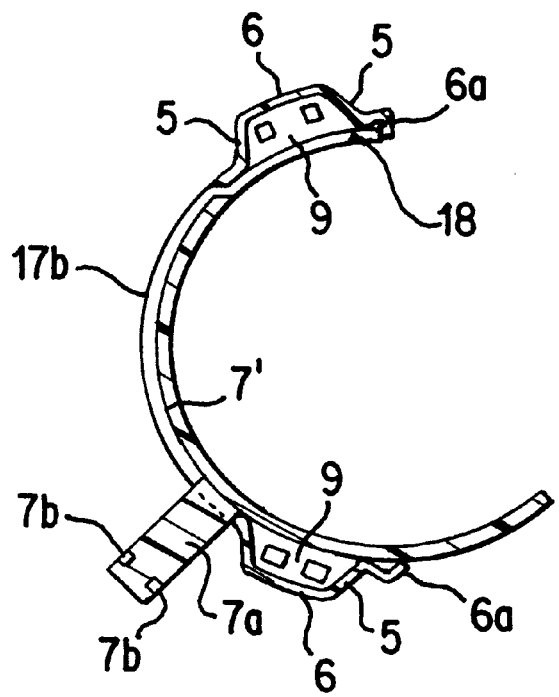

FIG. 9 the same as a horizontal longitudinal cross-section, the casing plate in a position of filling with an agent, before attaching the ring, the tablet container an the right hand side being open.

Figure 10:
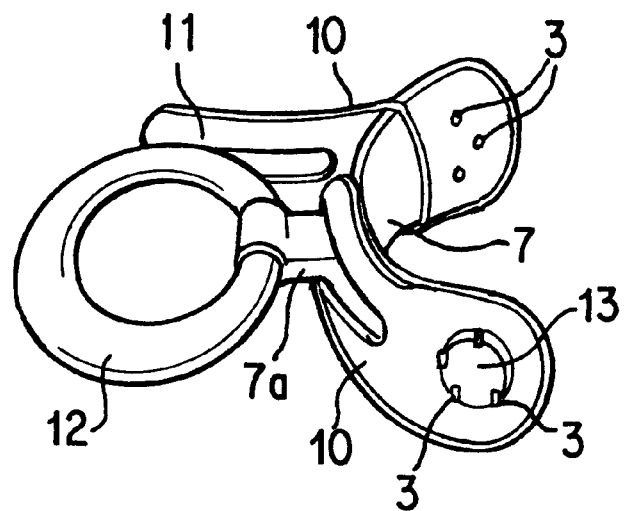

FIG. 10 illustrates a hard oral screen provided with elastic sheath containers seen from in front, at an angle from above.

Figure 11:
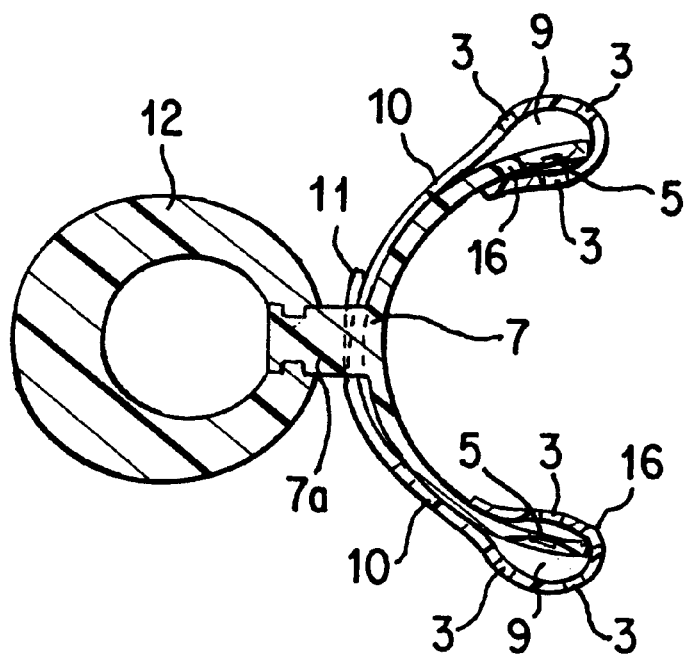

FIG. 11 the same as a horizontal longitudinal cross-section.

Figure 12:
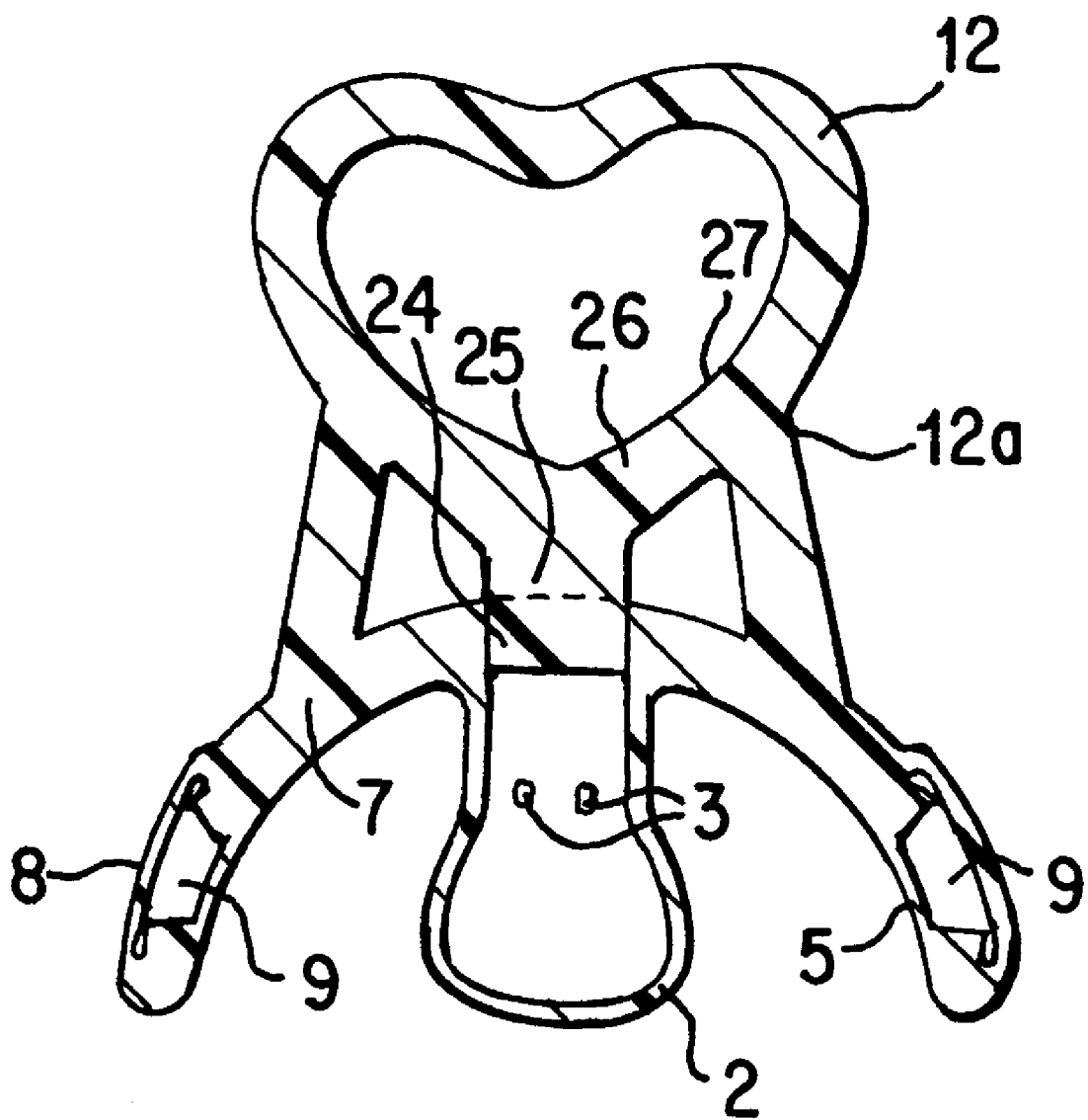

FIG. 12 illustrates a training oral screen (having a pacifier-like dispensing sucking piece) in a horizontal longitudinal cross-section.

Figure 1:
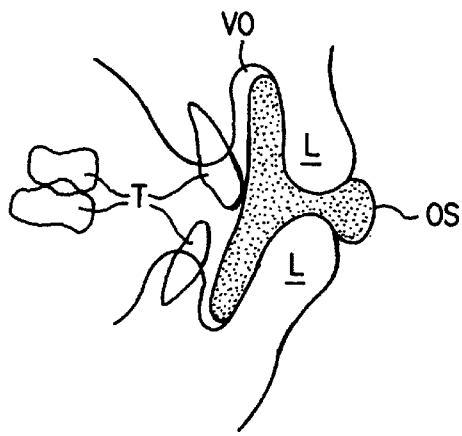
FIG. 1 illustrates in a schematic manner an oral screen in its place in the space between the lips and teeth.
Figure 2:
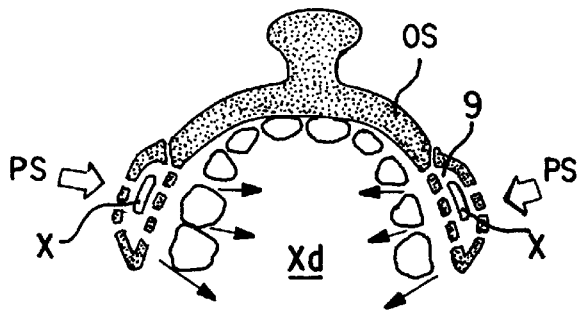
FIG. 2 illustrates the operation principle of an oral screen provided with dispensing containers in accordance with the invention.
Figure 3:
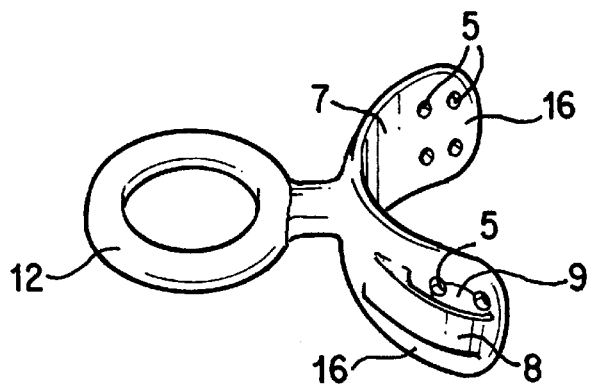
FIG. 3 illustrates an oral screen made from an elastic material seen laterally, at an angle from above.

The FIGS. 3 and 4 show an embodiment of an oral screen dispenser according to the invention, which is made from an elastic material. In this case the whole device with its frame 7, ring 12 and tablet fastening means, which in this case is a strip 8 extending over the tablet container 9, is made in one part from an elastic plastic, for which purpose a stiff silicone is suitable. The strip 8 can be loosened by straightening the arched end part 16 of the cheek flange. By simultaneously pulling the strip 8 to the side, a tablet strictly matching its recess 9 can be placed underneath the strip 8. When the end part 16 is not bent any longer, it strives at regaining its original arched form tightening the tablet in its place so that a small child cannot remove the same. The bottom of the tablet container 9 is provided with one or more holes 5. In the example, there are four boles 5 placed cylindrically on the outer periphery of the container 9, half outside the edge so that the parotid saliva flowing past the side edges of the fastening strip 8 into the container 9 can flow freely past the sides of the tablet which initially sealingly fills the bottom of the container, slowly dissolving the same, to the inner oral cavity.

The following examples illustrate embodiments made completely or partly from a hard plastic (for example an ABS plastic):

FIGS. 5–7 illustrate an oral screen dispenser, wherein pill casings form dispensing containers 9 mounted in the cheek flanges of the oral screen and provided with buccally opening hinged lids 6, the hinge part 14 being placed distally. In the cross-section through the plane of the middle seam 15 (FIG. 6), the left hand pill casing is seen with the lid 6 open. In the lid 6 and in the frame 7 in the bottom of the container 9, there are holes 5. A locking tongue 6a functions as a locking means for the lid 6, and the lid is opened by gripping and lifting the opening rim 6b.

The FIGS. 8-9 illustrate an oral screen dispenser formed by a sliding plate 7' and a caning cover 17. The sliding plate 7' is provided with a shaft 7a insertable through a mounting aperture 17a in the casing cover 17, the end part or which having recesses 7b into which a ring 12 is fastened. The sliding plate 7' is snap-shut into its groove or casing 18 in the casing cover, when the ring 12 is pulled in an outward direction. At this stage, the right hand tablet casing acting as a dispensing container 9, as seen from the direction of the child, and having a cover 6 with holes 5, is open for filling purposes. By pushing the shaft 7a of the sliding plate to the right hand edge of the sliding slot 17b in the casing cover 17, the left hand tablet casing opens for filling. In the center position of the shaft 7a, which is the normal position of the device in use, the containers 9 in a closed position, the sliding plate 7' is locked into place by means of elastic locking tongues 6a situated at the distal ends of the casing cover, a locking rim 7c in the shaft 7a preventing the sliding plate 7' from detaching from the groove 18 in the casing cover 17, if a pushing force were to hit the shaft 7a from the front. For cleaning purposes, the sliding plate 7' can be detached from the groove 18 in the casing cover by pushing the shaft 7a with rim 7c through the mounting aperture 17a inwards. Even in this case the parts do not detach from each other completely due to the ring 12. The ring 12 cannot be released from its recesses 7b by a child, but needs the force of a grown-up's fingers. In the sliding cover there are holes 5 at the tablet containers 9, through which the agent to be dispensed and dissolved primarily by the effect of the saliva from the glandula parotidea can affect the solar teeth region.

FIGS. 10 and 11 illustrate an oral screen wherein the frame 7 of the device is made from a hard plastics material and the dispensing containers with their fastening means are made from an elastic material (silicone, rubber). The dispensing container unit is a flat baglike sheath structure which forms a container 9 resembling the sucking piece of a pacifier, which is pulled, with the tablet 13 to be dispensed inside, over the end of the cheek flange 16 of the plate 7 and is tensioned tightly into place by stretching the loop 11 in the strap 10 of the container 9 facing the cheek, over the ring 12 in back of the shaft 7a. Sheaths are needed one for each cheek flange of the oral screen, the tablet recesses in the cheek flanges having in this example one smallish hole 5 made in their bottom. Saliva can freely flow through the holes 3 in the container 9 and the hole 5, as well as due to the lateral clearance of the sheath, through the container 9, inside and out.

As alternative solutions, the afore described individual containers 9 can be combined either from their loop straps on the cheek facing side, or so, that the whole surface of the oral screen facing the teeth is covered with a fastening collar means joining the sheaths into one piece having two sheaths.

FIG. 12 illustrates a training oral screen. A child can be trained to use an oral screen while being weaned from pacifier use by providing the oral screen frame 7, on its inside, with a pacifier-like sucking piece 2, for example a dispensing sucking piece. The sucking piece 2 can suitably be made in one piece with the oral screen, for example from soft vinyl, and it can be provided with holes 3 for the active agent, its opening opening up in the container 9. The opening is closed with a plug 24, the continuation part or shaft 25 of which joins two closing shafts 26 arranged substantially in a V-shaped manner with respect to each other and extending to the inside periphery 27 of the sides of the ring-shaped gripping device 12, 12a. The said construction effectively prevents the opening of the plug during use.

The pacifiers and the oral screens can be boiled. Thus the required hygienic level can be reached in domestic circumstances.

For a person skilled in the art it is evident that the invention is not restricted only to the examples shown above, but can vary within the scope of the appended patent claims.

REFERENCES

Arends J, Christofferssen J, Schuthof J, Smitz M T. Influence of xylitol on demineralization of enamel. Caries Res 1984, 18, 296–301

Darby F B. Appliance to prevent mouth breathing. Dent Cosmos 1890, 32; 214

Filler S J, Gregory R L, Michalek S M, Katz J, McGhee J R. Effect of immune bovine milk on *Streptococcus mutans* in human dental plaque. Arch Oral Biol 1991, 36, 41–7

Giebink G S. Preventing otitis media. Ann Otol Rhinol Laryngol 1994, 103, 20–3

Grenby T H. Advances in non-caloric sweeteners with dental health advantages over sugars. Proc Finn Dent Soc 1991, 87, 489–99.

Hamilton I R. Effects of fluoride on enzymatic regulation of bacterial carbohydrate metabolism. Caries Res 1977, 11, (suppl 1) 262–91

Harper D S, Loesche J. Inhibition of acid production from oral bacteria by fluoroapatite derived fluoride. J Dent Res 1986, 65, 30–3

Isokangas P. Ksylitolin käyttö kouluikäisten kariespreventiossa. Tieteellinen tausta. Fiksu tapa. Valtakunnallinen terveystapahtuma. STAKES, Helsinki 1994, 4–16

Kauppi M, Saarinen L, Käyhty H. Anti-capsular polysaccharide antibodies reduce nasopharyngeal colonization by *Haemophilus influenzae* type b in infant rats. J Infect Dis 1993, 167, 365–71.

Kilian M, Thylstrup A, Fejerskov O. Predominant plaque flora of Tanzanian children exposed to high and low water fluoride concentrations. Caries Res 1979, 13, 330–43

Kontiokari T, Uhari M, Koskela M. Effect of xylitol on growth of nasopharyngeal bacteria in vitro. Antimikrob Agents Chemother 1995, August 39(8), 1820–1823.

Laitinen S. Ristipurennat yleistymässä—missäsyy? (Crossbites becoming more general—where is the reason?) Suom Hammasläak L 1995, n:o 16, 896–901

Lenander-Lumikari M. Salivary peroxidase systems and lysozyme in defence against cariogenic microorganisms. Thesis. University of Turku 1992

Ma JK-C, Lehner T. Prevention of colonization of *Streptococcus mutans* by topical application of monoclonal antibodies in human subjects. Arch Oral Biol 1990, 35, Suppl 115S–122S Ma J K-C, Hunjan M, Smith R, Kelly C, Lehner T. An investigation into the mechanism of protection by local passive immunization with monoclonal antibodies against *Streptococcus mutans*. Infect Immun 1990, 58, 3407–14

Michalek S M, Gregory R L, Harmon C C, Kak J, Richardsson G J, Hilton T, Filler S J, McGhee J R. Protection of gnotobiotic rats against dental caries by passive immunization with bovine milk antibodies to *Streptococcus mutans*. Infect Immun 1987, 55, 2341–7

Mühlemann H, Regolati B, Marthaler T. The effect of rat fissure caries of xylitol and sorbitol. Helv Odont Acta 1970, 14, 48–50

Mäkinen K K. Biochemical principles of the use of xylitol in medicine and nutrition with special consideration of dental caries. Birkhäuser Verlag, Basel 1978

Mäkinen K K, Isokangas P. Relationship between carbohydrate sweeteners and oral diseases. Prog Food Nutr Sci 1988, 12, 73–109

Mäkinen K K, Scheinin AS. Xylitol and dental caries. Ann Rev Nutr 1982, 2, 100–20

Neeser J-R, Chambaz A, Del Vedovo S, Prigent M-J, Guggenheim B. Specific and nonspecific inhibition of adhesion of oral Actinomyces and Streptococci to erythrocytes and polystyrene by caseinoglycopeptide derivates. Infect Immun 1988, 56, 3201–8

Niemelä M. Risk factors and symptoms of acute otitis media in children. Dissertation. Acta Universitatis Ouluensis D Medica 324. Oulu University, Oulu 1994

Rölla G. Effects of fluoride on initiation of plaque formation. Caries Res 1977a, 11 (suppl 1), 243–61

Scheinin A, Mäkinen K K. Turku sugar studies I–XXI. Acta Odontol Scand (Suppl 70) 1975, 33, 1–351

Suhonen J. Mutans streptococci and their specific oral target. New implications to prevent dental caries? Schweiz Monatsschr Zahnmed 1992, 102, 286–291

Suhonen J, Sener B, Bucher W, Luk F. Release of preventive agents from pacifiers in vitro. An introduction to a novel preventive measure. Schweiz Monatsschhr Zahnmed 1994, 104, 946–51

Söderling E, Pihlanto-Leppälä A. Uptake and expulsion of $^{14}$C-xylitol by xylitol-cultured Streptococcus mutans ATCC 25175 in vitro. Scand J Dent Res 1989, 97, 511–19

Söderling E, Scheinin A. Perspectives on xylitol-induced oral effects. Proc Finn Dent Soc 1991, 87, 217–30

Touster O. Essential pentosuria and the glucuronate-xylulose pathway. fed proc 1960, 19, 977–83

Uhari M, Kontiokari T, Koskela M, Niemelä M. Br Med J 1996, 313, 1180- van Houte J, Aasenden R, Peebles T C. Oral colonization of Streptococcus mutans in human subjects with low caries experience given fluoride supplements from birth. Arch Oral Biol 1978, 23, 361–6

Varrela J, Alanen P. Voidaanko hampaiden asentovirheitä ehkäistä? (Can malpositions of the teeth be prevented?) Suom Hammasl L 1995, n:o 17, 951–4

Zickert I, Emilson C G. Effect of a fluoride-containing varnish on Streptococcus mutans in plaque and saliva. Scand J Dent Res 1982, 90, 423–8

We claim:

1. Intraoral administration device comprising:
    an elongated, substantially plate-like arcuate oral screen designed to conform to the teeth and intended to be positioned in a space between the teeth and the lips so that a first surface of the oral screen faces the lips and a second surface of the oral screen faces the teeth, and
    containers defined at opposite lateral end regions of said oral screen for an agent to be administered intraorally, said containers being adapted to allow free entrance of saliva into the containers and its exit therefrom.

2. The administration device according to claim 1, and further comprising a pacifier-like sucking piece attached to the second surface of the oral screen.

3. The administration device according to claim 2, wherein the sucking piece functions as a dispenser, is made in one piece with the oral screen from soft vinyl, and is provided with holes allowing free entrance of saliva, and wherein a base part of the sucking piece opening into the oral screen has a closable filling opening.

4. The administration device according to claim 3, wherein the filling opening is provided with a cover plug which, over at least two closing shafts arranged in a substantially V-shaped manner with respect to each other, joins an inside periphery of a gripping ring.

5. Administration system, comprising an administration device in accordance with claim 1, and at least one of the following active agents:
    a caries preventing agent,
    an agent preventing middle ear infection,
    an agent preventing the adhesion and/or accumulation of pathogens,
    a sweetening agent,
    an anti-inflammatory agent,
    an antibody,
    a remineralization agent, and
    an antibacterial enzyme.

6. The administration system according to claim 5, wherein the at least one of the active agents is formed into any one of a tablet, pill, powder, gel or impregnated fabric which fits the containers of the administration device.

7. The administration device according to claim 1, wherein the free entrance of saliva into the containers and its exit therefrom are provided by apertures or holes.

8. The administration device according to claim 1, and further comprising a gripping ring attached to the first surface of the oral screen and which extends outside the mouth in use.

9. The administration device according to claim 1, wherein the containers are openable for filling purposes.

10. The administration device according to claim 1, wherein each of the containers is formed by a recess in the oral screen and a cover covering at least part of the recess.

11. The administration device according to claim 1, and further comprising a gripping knob attached to the first surface of the oral screen and which extends outside the mouth in use.

12. Intraoral administration device comprising:
    an elongated, substantially plate-like arcuate oral screen designed to conform to the teeth and intended to be positioned in a space between the teeth and the lips, and
    containers for an agent to be administered intraorally, said containers being adapted to allow free entrance of saliva into the containers and its exit therefrom,
    wherein each of the containers is formed by a strip which is attached to a surface of the oral screen facing the cheeks and a recess extending in a cup-like manner from the surface.

13. Intraoral administration device comprising:
    an elongated, substantially plate-like arcuate oral screen designed to conform to the teeth and intended to be positioned in a space between the teeth and the lips, and
    containers for an agent to be administered intraorally, said containers being adapted to allow free entrance of saliva into the containers and its exit therefrom,
    wherein the administration device is made from an elastic material, and wherein the containers include strips which extend over recesses in the oral screen to close the containers and are made in one piece with the oral screen.

14. Intraoral administration device comprising:
    an elongated, substantially plate-like arcuate oral screen designed to conform to the teeth and intended to be positioned in a space between the teeth and the lips,
    containers for an agent to be administered intraorally, said containers being adapted to allow free entrance of saliva into the containers and its exit therefrom, and
    lids hinged to the oral screen and provided with locking tongues for attaching the lids in closed positions to the oral screen.

15. Intraoral administration device comprising:
    an elongated, substantially plate-like arcuate oral screen designed to conform to the teeth and intended to be positioned in a space between the teeth and the lips, and containers for an agent to be administered intraorally, said containers being adapted to allow free entrance of saliva into the containers and its exit therefrom, wherein the container comprises sheath structures made from an elastic material and slid over opposite ends of the oral screen, said sheath structures being in sealing engagement with the oral screen and provided with apertures.

16. Intraoral administration device comprising:

an elongated, substantially plate-like arcuate oral screen designed to conform to the teeth and intended to be positioned in a space between the teeth and the lips, containers for an agent to be administered intraorally, said containers being adapted to allow free entrance of saliva into the containers and its exit therefrom, each of the containers being formed as a sheath structure, a gripping ring attached to a surface of the oral screen facing the lips which extends outside the mouth in use, and a loop fastened to a rim part of the sheath structure which can be pulled over the gripping ring for fastening the sheath structure.

17. Intraoral administration device comprising:

an elongated, substantially plate-like arcuate oral screen designed to conform to the teeth and intended to be positioned in a space between the teeth and the lips, containers for an agent to be administered intraorally, said containers being adapted to allow free entrance of saliva into the containers and its exit therefrom, the oral screen comprising a casing cover with the containers arranged in lateral end regions of the casing cover and being provided, in its longitudinal direction, with a sliding slot extending from the center of the casing cover towards said lateral end regions, and a sliding plate slidably mounted in a groove in an inner surface of the casing cover allowing the containers to be opened for filling purposes, and a ring, attached to the sliding plate, slidably mounted in the sliding slot and extending outwards from the casing cover, and the casing cover and the sliding plate including a lock.

* * * * *